United States Patent [19]

Renirie et al.

[11] Patent Number: 5,741,211
[45] Date of Patent: Apr. 21, 1998

[54] SYSTEM AND METHOD FOR CONTINUOUS MONITORING OF DIABETES-RELATED BLOOD CONSTITUENTS

[75] Inventors: Alexis C. M. Renirie, Berg En Dal; Richard Houben, Bergen Terblijt; Frank van Leeuwen, Maastricht, all of Netherlands

[73] Assignee: Medtronic, Inc., Minneapolis, Minn.

[21] Appl. No.: 548,784

[22] Filed: Oct. 26, 1995

[51] Int. Cl.[6] .................................................. A61B 5/00
[52] U.S. Cl. ........................ 600/300; 600/509; 128/920
[58] Field of Search .................................... 128/630, 668, 128/670, 696, 700, 695, 702, 703, 705, 920; 607/6, 72, 22, 25

[56] References Cited

FOREIGN PATENT DOCUMENTS

4483571/14  7/1988  U.S.S.R. .

OTHER PUBLICATIONS

Parrish, A. et al., "A Relationship Between Electrocardiographic Changes and Hypokalemia in Insulin–Induced Hypoglycemia," American Heart Journal, Jan. 31, 1952, pp. 815–820.

Ostrander, Leon D., "Electrocardiographic Changes After Glucose Ingestion," Cirulation, vol. XXX, Jul. 1964, pp. 67–76.

Zierler, K., "Effect of Very Small Concentrations of Insulin on Forearm Metabolism. Persistence of Its Action on Potassium and Free Fatty Acids Without Its Effect on Glucose," Journal of Clinical Investigation, vol. 43, No. 5, 1964, pp. 950–961.

Riley, Charles P., "Electrocardiographic Effects on Glucose Ingestion," Arch. Intern. Med., vol. 130, Nov. 1972, pp. 703–707.

Garcia, Mariano J. et al., "Morbidity and Mortality In Diabetics In the Framingham Population," Diabetes, vol. 23, No. 2, Feb. 1974, pp. 105–111.

Ducimetiere, P. et al., "Relationship of Glucose Tolerance to Prevalence of ECG Abnormalities and To Annual Mortality From Caridovascular Disease: Results of the Paris Prospective Study," J. Chron. Dis., vol. 32, pp. 759–766.

Flügelman, Moshe et al., "Electrocardiographic Patterns In Diabetics Without Clinical Ischemic Heart Disease," Israel Journal of Medical Sciences, vol. 19, 1983, pp. 252–255.

Heine, R.J., "A Comparison of the Effects of Semisynthetic Human Insulin and Porcine Insulin on Transmembrane Ion Shifts and Glucose Metabolism During Euglycaemic clamping," Acta Endocrinologica, 1984, 106:241–247.

Butler, William J. et al., "Mortality From Coronary Heart Disease in the Tecumseh Study," American Journal of Epidemiology, vol. 121, No. 4, 1985, pp. 541–547.

(List continued on next page.)

Primary Examiner—Jennifer Bahr
Assistant Examiner—Bryan K. Yarnell
Attorney, Agent, or Firm—Michael J. Jaro; Harold Patton

[57] ABSTRACT

A system and method for sensing and providing an indication of one or more diabetes-related blood constituents of a patient, the system being based upon an ECG sensor which processes patient ECG signals, either surface, or intracardiac or epicardial, for determining a measure of a blood constituent such as insulin or glucose, or both insulin and glucose. The system has processing capability for correlating selected parameters of the ECG signal with patient blood insulin or blood glucose, to provide the insulin or glucose level. Additionally, the system is provided with input capability for enabling the patient to input data such as the time of meal intake, which is representative of glucose intake, which data is incorporated in making a determination of patient insulin need. The system can be in a first external wearable embodiment, or in a second implantable embodiment which utilizes a pacing-type lead for picking up intracardiac or epicardial signals. In either the wearable or implantable embodiment, the output response may be simply an indication of patient insulin and/or glucose need provided by an external display, and may also include automatic control of insulin injection to the patient.

44 Claims, 4 Drawing Sheets

OTHER PUBLICATIONS

Tuomilehto, Jaakko et al., "Prevalence of Ischaemic ECG Abnormalities According to the Diabetes Status in the Population of Fiji and Their Associations With Other Risk Factors," *Diabetes Research and Clinical Practice*, 5 (1988), pp. 205–217.

Dedrick, R.F. et al., "What Do Statistics Really Tell Us About the Quality of the Data From Self–Monitoring of Blood Glucose," Diabetic Medicine, 1989:267–273.

Yang, Qi, "Signal–Averaging Electrocardiogram in Patients With Diabetes Mellitus," JPN. Heart J., Jan. 1990, pp. 25–33.

Research Disclosure No. 22728, "Method of Measuring Blood Glucose Level by Sensing Evoked Action Potentials in Peripheral Nerve," Roy Testerman, Medtronic, Inc.

Heinemann, Lutz, "Hypoglycomia Detection by ECG Recording?" Diabetes Care, vol. 18, No. 1, Jan. 1995.

SYSTEM AND METHOD FOR CONTINUOUS MONITORING OF DIABETES-RELATED BLOOD CONSTITUENTS

BACKGROUND OF THE INVENTION

This application relates to a system and method for continuous monitoring of patient diabetes-related blood constituents and, in particular, a monitoring system and method utilizing patient ECG for determining blood insulin and/or blood glucose.

The treatment of insulin-dependent diabetes mellitus (IDDM) has received a great deal of attention for several decades, but remains a significant challenge. Comprehensive diets and injective insulin administration, combined with glucose level determination multiple times a day, provide a good degree of metabolic control, but are short of being optimum, also induce considerable patient discomfort. The injected insulin does not enter the circulation directly, resulting in a delayed and reduced effect in bringing the plasma glucose level down to acceptable values. The increased and prolonged hyperglycemic and/or hypoglycemic periods contribute to chronic complications. Occular complications like cataract and retinopathy occur in approximately 50% of such patients after ten years. Severe nephropathy, neuropathy, and gangrene of the feet and skin complications are frequently observed.

A relationship between diabetes mellitus and coronary heart disease has long been suggested. See Garcia, M. J. et al., "Morbidity and Morality in Diabetics in the Framingham Population: Sixteen Year Follow-Up Study," *Diabetes*, 23:105–11 (1974); Fein, F. S., "Heart Disease In Diabetes," *Cardiovasc. Rev. Rep.*, 3:877–93 (1982); "Relationship of Glucose Tolerance to Prevalence of ECG Abnormalities and to Annual Mortality From Cardiovascular Disease: Results of the Paris Prospective Study," Ducimetiere et al., *J. Chron. Dis.*, Vol. 32, pp. 759 to 766 (1979). Additionally, there has been a recognition of a correlation between a patient ECG and blood potassium level, and variations in the ECG following introductions of insulin. See the paper of Heine et al., *Acta Endocrinologica* 1984, 106:241–247.

The field of glucose monitoring is an extremely active one. Its importance lies in indicating to the diabetic when and how much insulin should be taken. Ideally, glucose monitoring would be continuous and non-invasive. With an accurate continuously monitoring glucose sensor, information would constantly be available, either to signal a condition of hyperglycemia or hypoglycemia, or even direct and enable a closed loop system by which insulin would be automatically delivered so as to keep glucose levels close to normal physiological levels. Such a system would reduce chronic complications and provide an obvious increase in quality of life for IDDM patients.

Most glucose sensors presently in common use are based on electrochemical methods such as the electroenzymatic method where blood glucose is oxidized under glucose-oxidase control, producing gluconic acid and hydrogen peroxide. By using this enzymatic reaction as a first stage, the problem is reduced to a measurement of used oxygen or produced hydrogen peroxide, i.e., amperometric method. Alternately, the produced gluconic acid can be determined directly (potentiometric method). However, both of these sensor types suffer from stability problems. Optical glucose sensors have been tried, but for several reasons are not feasible for longterm continuous monitoring, and particularly not for an implantable glucose monitor.

We have conducted tests which confirm that in non-diabetic subjects, ECG changes correlate with blood glucose. These changes result from the change in the blood potassium concentration due to insulin mediated cellular potassium uptake. In these subjects, we have found a correlation between selected ECG parameters, notably QRS and T wave mean and RMS, and both plasma glucose and insulin. This situation applies to patients with non-insulin diabetes mellitus (NIDDM). However, for insulin dependent diabetes mellitus patients where insulin is below a basal value, plasma glucose and ECG are not coupled. Rather, for these patients glucose uptake is not followed by a pancreatic insulin response, and this is reflected by a substantially unchanged ECG following glucose uptake.

There has thus been and remains a longstanding problem in providing a glucose monitor or any monitor to indicate insulin need, which can carry out monitoring functions substantially continuously over long periods of time; does not require user activation or intervention; and can be miniaturized so as to either be worn externally or even implanted within a patient. In contrast to prior an detectors, the basic approach to this problem as manifested in the subject invention has been to design a sensor utilizing ECG signals, and to derive selected parameters from the ECG which provide an accurate and reliable indication of insulin. Although there have been literature articles that disclose variations in ECG signals of diabetes in certain circumstances, there has been no disclosure or suggestion of a system using ECG signals for continuous sensing of blood insulin and/or glucose, or such a system that could be worn by a patient or implanted. In particular, there remains a vital need for a system which would reliably provide continuous monitoring, and thus tracking of blood constituents from which insulin need can be determined, i.e., insulin and glucose, and which can indicate that need, and even be a reliable basis for an automatic insulin delivery system.

The basis of the sensor of this invention is based on our observation of insulin/glucose-induced ECG changes. In a non-diabetic subject, a glucose load, as results from food intake, leads to an increase in plasma glucose. In turn, the pancreas produces an increase in blood insulin. Following an increase in insulin, there is a cellular membrane change which results in infusion of potassium into the cells, and a subsequent decrease in blood potassium along with glucose uptake. The lowered extracellular potassium, or blood potassium, shortens the cardiac monophasic action potential, and produces a steeper monophasic action potential upstroke. This in turn results in observable ECG changes, such as the development of U-waves, ST segment depression, and in particular a shortening of the T wave amplitude and a small increase in the R wave.

SUMMARY OF THE INVENTION

We have determined that the ECG is a continuous indicator of blood insulin, particularly where certain parameters of the ECG are captured and processed. As used here, the term "continuous" means ongoing and updated periodically. Thus, a continuous sensor as used here refers to a sensor which recalculates blood insulin every cardiac cycle, every predetermined number of cycles, or periodically at given time intervals such as every 15 minutes, every 30 minutes, every hour, etc. Further, either a surface ECG or an intracardiac ECG can be used for determining insulin, and can be used as part of a closed loop system for controlling insulin delivery to the patient. A closed loop control system is directly controlled by continuous measurement of present insulin concentration in the body, and by extrapolating insulin need based on recent insulin changes. Such a system basically consists of three components, i.e., the insulin sensor, an insulin delivery pump, and an implementation of the control strategy which is suitably microprocessor based and/or implemented using dedicated electronics. Alternately, the invention may comprise an open loop control system in which the insulin delivery is not feedback controlled by an on-line insulin level determination. Rather, in an open loop system insulin delivery is based on a predetermined or preprogrammed schedule. It has been established that in a healthy person, the insulin levels are elevated even before the blood glucose level rises, due to neural factors and the involvement of gut hormone levels. During meal periods, open loop systems perform better than closed loop systems, due to the capability of starting the insulin rate increase during and even before meal ingestion. Accordingly, it is anticipated that the invention may be adapted to a system which is closed loop controlled generally, but open loop controlled in accordance either with a programmed time schedule, or in response to external programming by the patient.

Accordingly, it is a primary object of this invention to provide a system and method for continuous sensing of blood insulin, which is adaptable for being worn by an ambulatory patient, or implanted in a patient. The object of this invention is further to provide a sensor which discriminates changes in blood insulin based upon processing of ECG signals, and which provides a reliable correlation between monitored ECG parameters and insulin level. Accordingly, there is provided a system which utilizes electrodes for continuously sensing the patient ECG signals, and signal processing capability for discriminating selected portions from the ECG signals, including the QRS and T-wave. The discriminated portions are further signal processed to determine predetermined parameters selected from a group of parameters including QRS and T wave absolute mean and RMS values, and QRS, Q-T and RR intervals. The system has data storage for storage of basal values of the preselected ECG parameters, and further processing capability for comparison with the stored basal value in order to continuously determine a measure of blood glucose and/or blood insulin.

The monitoring portion of the system, i.e., the sensor, may be combined with a wearable case, providing either a continuous or on-demand output of insulin levels, as well as a stored history of the patient's insulin levels. In another embodiment, the sensor is part of an implantable system, open or closed loop, which is combined with an insulin pump and control means for controlling injections of insulin to the patient's blood stream as a function of monitored glucose level.

In addition, the system and method of this invention include utilization of the ECG sensor for determining blood glucose level under conditions where a correlation between selected ECG parameters and blood glucose is valid. Thus, in diabetic patients who are not insulin dependent, there is a significant correlation, i.e., changes in the ECG reflect changes in blood glucose. Determination of blood glucose may be made based upon different portions or parameters taken from the ECG. Additionally, the system of this invention incorporates the capability of permitting the patient to input data concerning glucose intake. Thus, for either an external (wearable) or implantable system, an exogenous insulin event can be inputted by the patient, such as by simply pressing one keypad to register the event and the time, or by inputting numeric data contained more information as to the insulin dose. In another embodiment of the invention, a software-constructed patient model of insulin and glucose changes is used, along with the sensed or inputted insulin and glucose data, to provide indications of insulin, as well as glucose need. Further, the model may be used to provide direct closed loop and/or open loop control of an insulin pump for automatically providing insulin to the patient.

DESCRIPTION OF THE PREFERRED EMBODIMENTS

Figure 1:
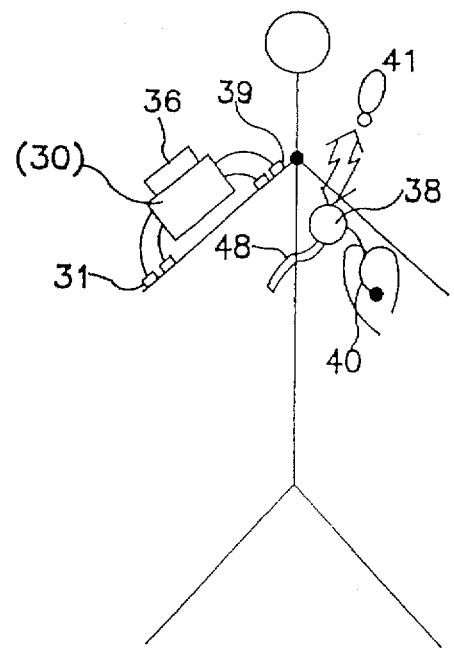
FIG. 1 is an overview perspective schematic illustrating a patient with either a wearable pack, or halter, which carries the system apparatus of this invention, or an implanted embodiment of the system of this invention.

Referring now to FIG. 1, there is shown a schematic representation of a patient with either a wearable pack 30 which houses a system in accordance with this invention, or implantable closed loop system apparatus 38 embodying the invention. In the case of a wearable package 30, it is adapted to be attached to the patient at a convenient and medically optimal position. The package has connections to electrodes 31 for detecting the ECG in a known manner. The electrodes may be conventional skin surface electrodes, or may be subcutaneous electrodes. Also shown schematically is an insulin flow path 39, comprising a delivery tube or like means for controlled transport of insulin to the patient from an insulin reservoir contained within housing 30. Also illustrated is input/output element 36, for inputting data to the system, as through a keyboard, and for displaying data.

Alternately, for an implantable embodiment of this invention, there is shown an implantable apparatus 38, having a lead 40 for insertion into the patient's heart to acquire intracardiac or epicardial ECG signals, and a pump output 48. Note that either the wearable glucose monitor system or the implantable system suitably comprise a microprocessor and ECG signal processing hardware and software, as discussed more fully below. Either embodiment can comprise any combination of hardware or software. The wearable system, for example, can employ dedicated hardware for implementing the signal processing.

Figure 2B:
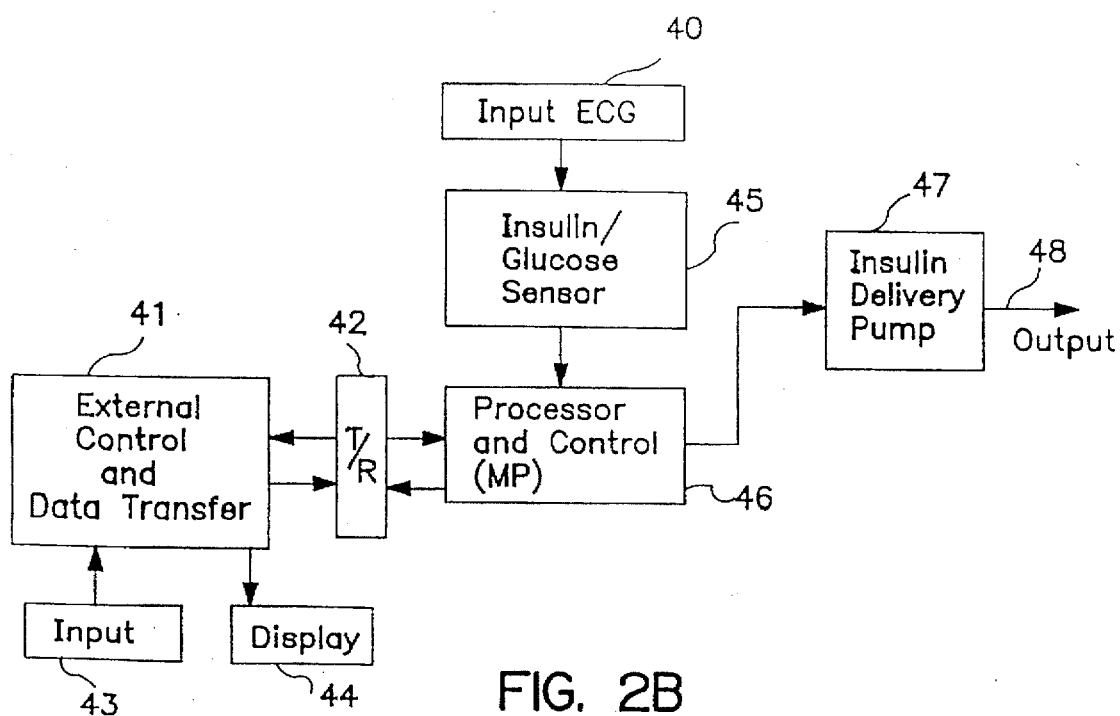
FIG. 2B is a block diagram of an implantable system utilizing the ECG-based sensor of this invention.
Figure 2A:
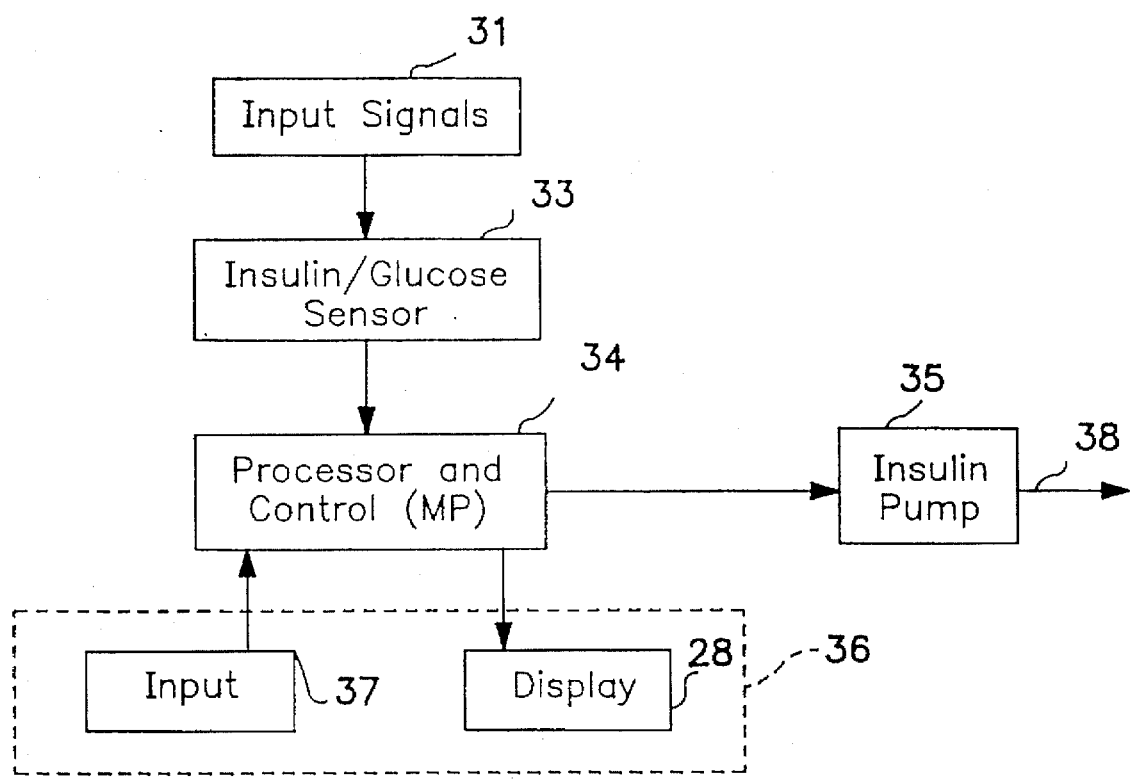
FIG. 2A is a block diagram of a wearable system utilizing the ECG-based sensor of this invention.

Referring now to FIG. 2A, there is shown a block diagram of an external, wearable embodiment of the system of this invention. As set forth above, a closed loop glucose control system in accordance with this invention is directly controlled by continuous measurement of insulin, or insulin and glucose concentration in the body, and consists basically of sensor 33, insulin delivery pump 35, control 34, and input/output 36. The sensor 33 is described in detail below, and derives its input from ECG electrodes. The insulin delivery pump 35 provides insulin to the patient through an insulin delivery catheter 39, and the pump must be capable of delivering insulin with flow rates in the range of 10–50 ul/min. Various types of insulin pumps are presently available as candidates for this system, as well as several forms of stable insulin in high concentration. It is, of course, desirable to have a capacity which provides an extended refill. The delivery pump is controlled by the control shown at block 34 which, as discussed above, suitably comprises a microprocessor and any desired combination of dedicated hardware and/or software. Control block 34 takes its primary input from sensor 33, and generates control signals for delivery of insulin as a function of monitored blood insulin, or blood insulin and glucose level. Control 34 may also be programmed and/or controlled through input 37, which may be a simple keyboard or other input elements suitable for the wearer to provide inputs, e.g., when a meal has been ingested, or insulin has been taken. Display 28 may be provided by any suitable display and/or auditory means, by which the wearer can be informed of blood insulin and/or glucose level. Indeed, as a first simple embodiment, it is anticipated that the wearable device will not incorporate controlled insulin delivery, but only provide blood constituent readings to the wearer.

FIG. 2B illustrates a block diagram of the primary components of a system which includes implantable apparatus 38. Implantable apparatus 38 incorporates the necessary housing, or container, such as known in the pacemaker art, for making the apparatus adaptable to being implanted in the patient. Connected to it is a lead 40, providing the input signals, which is similar to pacing leads which are commonly used, and which pick up patient intracardiac or epicardial signals in a known manner. These signals are inputted into a sensor 45, which is adapted to extract information from the ECG signals so as to sense insulin, and/or glucose, as discussed in more detail below. The output of this sensor is transferred to processor and control block 46, which suitably contains a microprocessor, which processes the insulin and/or glucose information to derive control signals for controlling insulin delivery pump 47. Pump 47 provides its output through a catheter or other flow device 48. For an implantable embodiment, it is desirable to have an insulin capacity on the order of over 100 days, and preferably up to years. The longevity of available pumps for use in this system is estimated to be up to about three years. The implantable apparatus 38 also has a transmit/receive block 42, which is in communication with external device 41. Element 41 provides for transfer of control and other programming data, by conventional electromagnetic means as utilized in the pacemaker art. It also incorporates an input 43, such as a standard dialing keyboard, for receiving input data from the patient or from a physician. This data may be in the form of numerical data representative of amounts and time of glucose ingestion and/or insulin. The external apparatus also comprises a display 44, such as a typical liquid crystal display, for outputting numeric and other information relating to sensed insulin level, or insulin and glucose level, as well as data indicative of extrapolated time for needing insulin and/or glucose intake. It is to be noted that FIG. 2B shows a closed loop system. Such a system for insulin delivery may also be at least in part open loop, in that it may provide controlled insulin delivery solely as a function of inputted data concerning when the patient has ingested food, i.e., glucose intake. Also, another anticipated embodiment utilizes the implantable apparatus only for deriving data concerning diabetes-related blood constituents to the external display, i.e., does not contain an insulin pump.

Figure 3:
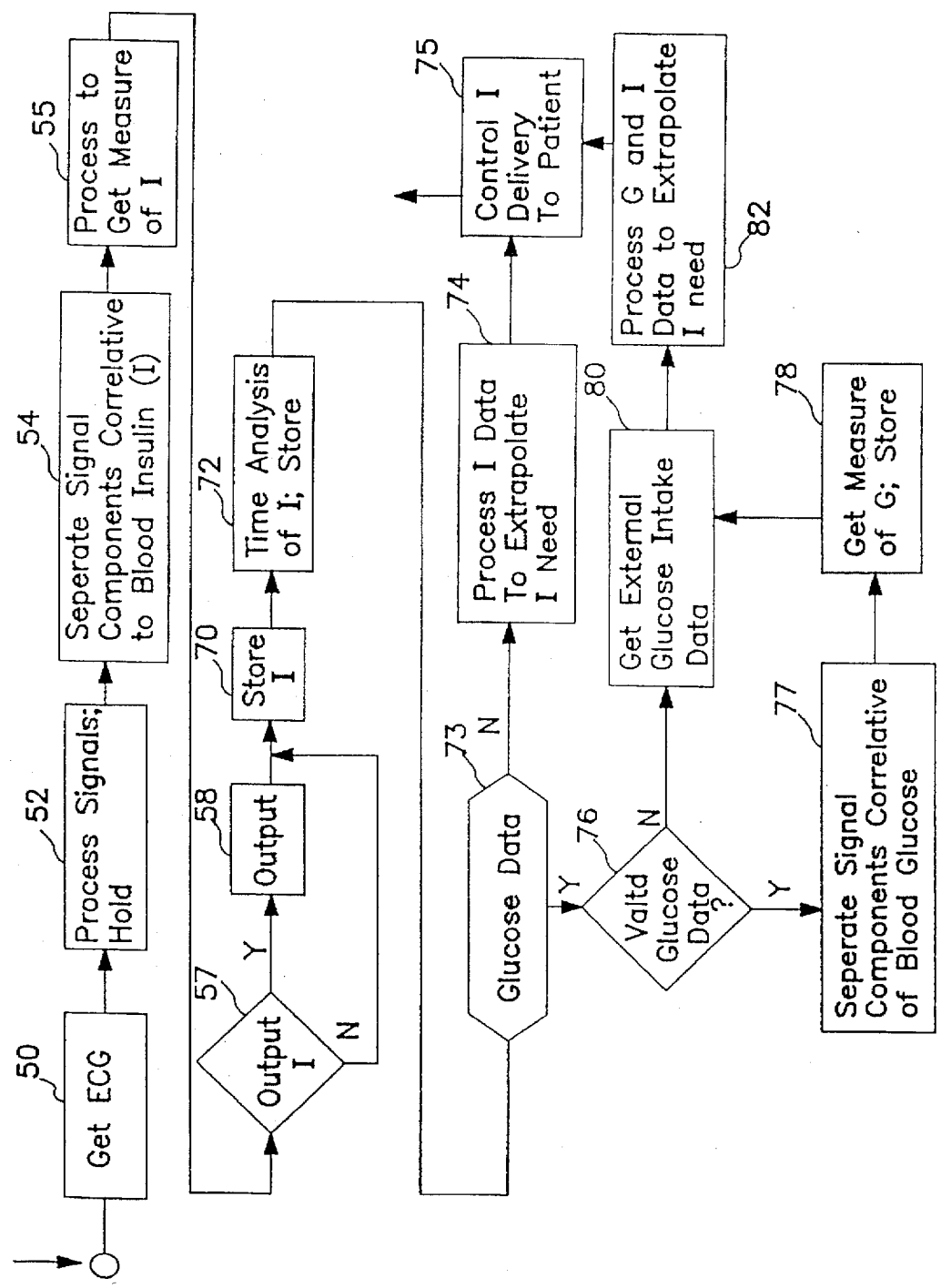
FIG. 3 is a flow diagram indicating the primary processing and control steps provided for in the system and method of this invention.

Referring now to FIG. 3, the flow diagram is representative of the primary steps taken in either an external, wearable system, or a system including an implantable apparatus. It is to be noted that, set forth above, either the wearable or implantable system can act simply as just a sensor with an output indication and need not incorporate any form of controlled insulin delivery. Thus, the scope of the invention may comprise all or just some of the steps and features set forth in FIG. 3. Further, it is to be noted that in a preferred embodiment of either the wearable or implantable system, many of the steps illustrated in FIG. 3 are carried out under microprocessor control, and as such are software steps.

At block 50, the system gets ECG signals, either surface ECG, or in systems having a lead extending into the patient's heart, intracardiac or epicardial ECG signals. It is to be noted that the wearable device could, under certain temporary circumstances, be combined with a temporary lead to provide intracardiac signals. At block 52, the ECG signals are processed to verify sensing of actual patient beats, filter out extraneous signals, etc. The signal information is suitably transformed into digital form, and held in buffer memory. At 54, the signals are processed to separate out predetermined components, or parameters, that correlate the two blood insulin (I) and possibly also blood glucose (G). These signal components, or parameters, include but are not limited to QRS and T wave amplitude and intervals, and Q-T and RR intervals. As noted above, different signal components may exhibit different correlations with patient insulin and/or glucose. Information concerning such correlation can be obtained by a physician through prior testing and stored in the system, for use in separating out selected signal parameters. At block 55, the selected signal parameters are processed to get a measure of insulin. It is to be noted that steps 52, 54 and 55 are discussed in greater detail in connection with the flow diagram of FIG. 4.

Following obtaining a measure of blood insulin, at block 57 there is a determination as to whether to provide an output of the insulin level, i.e., provide an output at display 28 or 44. If yes, the output step is performed at block 58. The routine then proceeds to block 70, and stores the insulin data. At block 72, there is a time analysis of the insulin, e.g., the time derivative may be obtained and stored, as well as incremental changes in insulin over predetermined time intervals, i.e., prior 15-minute, 30-minute or one-hour segments. At 73, it is determined whether the system is programmed to process glucose data, i.e., either sense or receive an input concerning patient glucose data. If no, meaning that the system is operating based only on insulin data, the insulin data is processed at 74 to extrapolate a patient insulin need. Note that, although not illustrated, the system may be adapted to receive an input from the patient concerning external injection of insulin, which data would also be used in processing future insulin need. The processing at 74 includes the time analysis data compiled at 72 in extrapolating insulin need. This extrapolated need is preformed cyclically and continuously, either every cardiac cycle, or periodically on the basis of batch data representative of a predetermined number of cardiac cycles. At 75, control of insulin delivery to the patient is performed, as a function of the control signals from block 74.

Returning now to 73, if the system is programmed to include glucose data, the next step, illustrated at 76, is to determine whether there is valid glucose signal data. As discussed above, the ECG data may or may not correlate to blood glucose level, depending upon the patient type and degree of diabetes. This validity determination may be programmed into the device, either the wearable or implantable device, so that the system is adaptable to consider the signal data for purposes of determining glucose only if validated by the physician. If the data is valid, at 77 the system separates out those predetermined signal components which are correlative of blood glucose. Then, at 78, these components are processed to obtain a measure of blood glucose, which measure is stored. After this, or after no answer to the validity question at block 76, at 80 the system gets external glucose intake data, if there is any. Thus, if the patient has inputted information indicating a meal, data concerning the time of such meal, which represents glucose intake, is obtained from memory. This glucose data, along with stored insulin data, is processed at 82 to extrapolate insulin need. This processing step is similar to that undertaken at 74, except that extrapolation of insulin need is performed as a function of both insulin and glucose data, or only glucose if the sensor is programmed to detect only glucose. The result of this processing is the generation of a control signal which is used to control insulin delivery, as shown at block 75.

Figure 4:
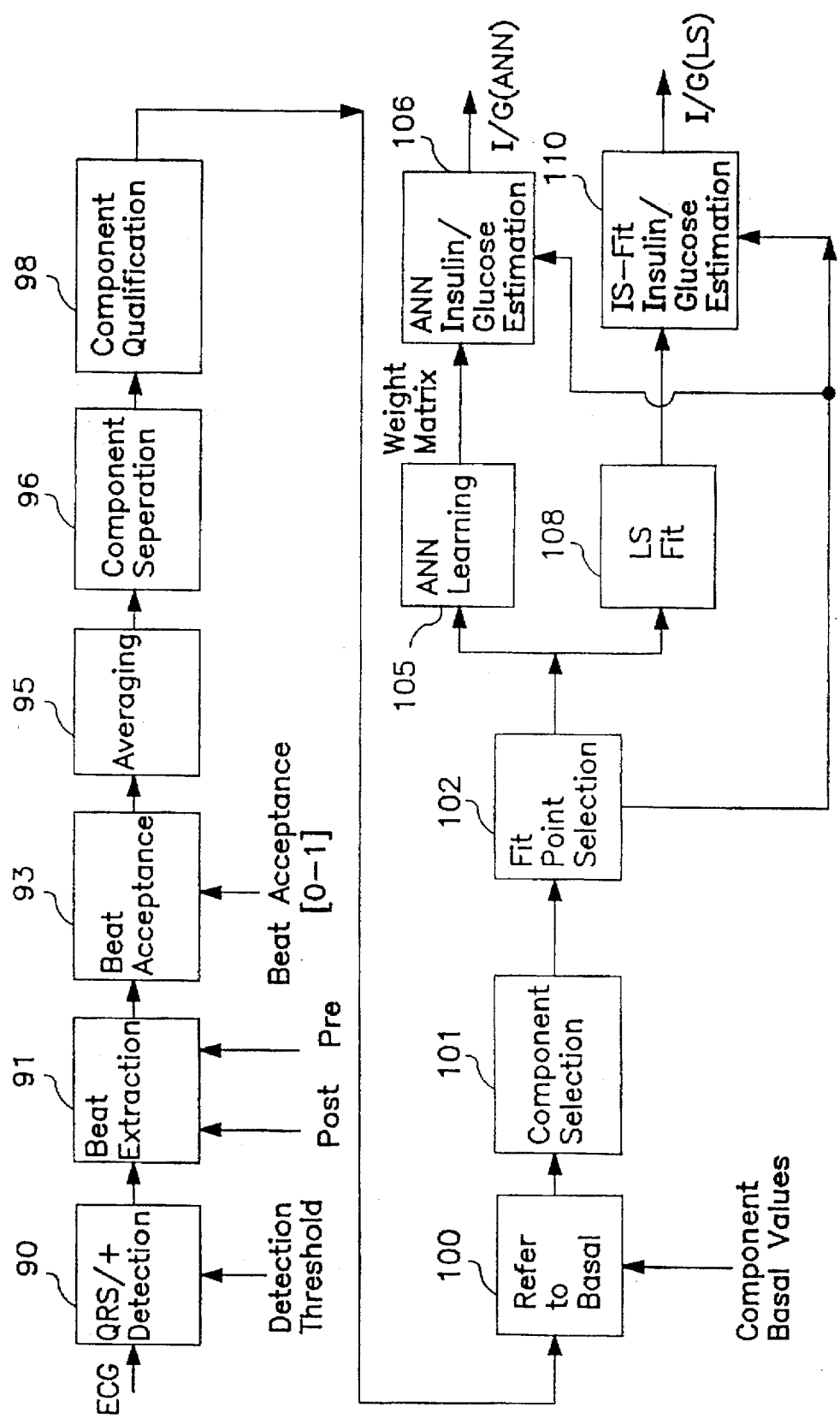
FIG. 4 is a flow diagram of more detailed steps taken in processing ECG signals to derive blood constituent data.

Referring now to FIG. 4, there is shown a block diagram representing in some detail the steps taken to process ECG signals in order to make an insulin or glucose determination. Most of the steps are performed under software control, but are susceptible to an embodiment incorporating any degree of dedicated hardware and software. At block 90, the incoming signal is processed to reduce noise, electro-magnetic interference and baseline drift. Next, to detect QRS and/or T-wave components, the signal-velocity is compared to a detection threshold in order to detect the presence of one or more selected components, e.g., the QRS and/or the T wave component. Although the T wave may be included in the signal analysis, for purposes of discussion in connection with this figure, the discussion will be limited to QRS signal analysis.

Continuing to block 91, the step of beat extraction is indicated, based on "post" and "pre" timing signals to delineate the cardiac beat. These timing signals are calculated based upon a time window within which the signal QRS signal is expected to appear. The extracted signal is then analyzed at 93, as by comparing it to a standard waveform, and either accepted or not. Following this, at block 95 the cardiac beat characteristics are averaged. For example, the signal data may be averaged over a predetermined number of beats, such as 100, to avoid randomness and reduce respiratory modulation below acceptable limits thereby reducing false indications. Following this, at block 96, the signal is further separated into components, i.e., portions of the signal, such as the QRS start and end, T wave start and end, Q-T interval, RR interval, PQ interval, etc. Following this, at 98, the step of component quantification is undertaken, wherein the signal processing, preferably under microprocessor control, quantifies potential parameters such as QRS width; QRS absolute mean value; QRS RMS; T-wave absolute mean and RMS; T-wave width; QT interval; and RR interval. At block 100, each quantified component, or parameter is referenced to a basal value previously determined and inputted into the system. Following this, at 101 component selection is made. Thus, for determination of blood insulin level, in a presently preferred embodiment, QRS and T wave amplitudes are selected. At block 102, a fit point selection is made, for use in correlating the component or parameter data to the estimated insulin or glucose level. The component data can be analyzed either by an artificial neural network (ANN) approach, as shown at blocks 105 and 106, or by a least squares fit, as indicated at blocks 108 and 110.

As used herein, ECG encompasses the Vector Cardio Gram (VCG), which is an ECG—derived signal. As is shown in the art, it is calculated from 3 ECG leads in a 3D plane or two ECG leads in a 2D plane, e.g., lead I and lead II. The VCG signal enables examination of the magnitude of the vector only, instead of both phase an magnitude; this reduces the effect of respiration. Processing the ECG signals to get the VCG can be done, for example, as part of the processing illustrated at 52.

What is claimed is:

1. System apparatus for providing an indication of at least patient blood insulin, comprising:

ECG sensor means for obtaining signals representative of the patient ECG, signal processing means for processing said ECG signals to provide first parameter data indicative of the patient's blood insulin level, wherein the signal processing means include means for comparing the sensed ECG signals against a reference value, and response means for providing a response as a function of said data.

2. The system apparatus as described in claim 1, wherein said response means comprises means for outputting an indication of the patient's blood insulin level.

3. The system apparatus as described in claim 1, wherein said system apparatus is implantable in said patient and said response means comprises pump means for injecting insulin into said patient as a function of said insulin data.

4. The system apparatus as described in claim 1, comprising a wearable housing for housing said apparatus and adapted to be worn by a patient, and wherein said response means comprises output means for providing an output signal receivable by said patient, said output signal being representative of the patient's insulin level.

5. The system apparatus as described in claim 1, wherein said signal processing means further comprises glucose means for processing said ECG signals and obtaining second parameter data indicative of the patient blood glucose level.

6. The system apparatus as described in claim 5, wherein said signal processing means further comprises analyzing means for analyzing said insulin and glucose data, and additional response means for providing a response as a function of said analyzed insulin and glucose data.

7. The system apparatus as described in claim 1, comprising keyboard input means for inputting data representative of patient glucose intake.

8. A system for providing an indication of blood insulin level of a patient, comprising ECG sensor means for sensing ECG signals of said patient, processing means for processing said ECG signals and obtaining therefrom a measure of patient blood insulin, wherein the processing means include means for comparing the sensed ECG against a reference value, and output means responsive to said insulin measure for outputting an indication of patient insulin level.

9. The system as described in claim 8, comprising an implantable housing for housing said system within said patient.

10. The system as described in claim 8, wherein said signal processing means comprises parameter means for separating out predetermined parameters of said patient ECG which correlate to patient blood insulin level.

11. The system as described in claim 8, comprising storage means for storing patient blood insulin levels, and wherein said signal processing means further comprises extrapolation means for extrapolating anticipated time of insulin need as a function of said stored patient blood insulin levels.

12. The system as described in claim 8, further comprising second processing means for processing said ECG signals and obtaining therefrom an indication of patient blood glucose.

13. The system as described in claim 12, further comprising delivery means for delivering insulin to the patient, and control means for controlling said delivery means to provide indicated insulin in response to indicated patient insulin and glucose levels.

14. A system for determining insulin need of a diabetic patient, comprising
ECG sensing means for sensing the patient ECG and deriving therefrom an indication of patient blood insulin level,
glucose input means for inputting data indicative of patient glucose intake,
processing means for determining patient insulin need as a function of said indicated blood insulin level and said glucose intake data, wherein the processing means include means for comparing said indicated blood insulin level against a reference value, and
response means for outputting an indication of said determined patient insulin need.

15. The system as described in claim 14, wherein said ECG sensing means comprises first processing means for processing ECG signals and deriving therefrom selected parameter data.

16. The system as described in claim 15, wherein said ECG sensing means comprises second processing means for determining time variations of selected ECG parameters and for calculating anticipated insulin need as a function of said variations.

17. The system as described in claim 14, wherein said glucose input means comprises an input terminal adapted to enable said patient to enter said glucose intake data.

18. The system as described in claim 17, wherein said input means comprises time means for storing data representative of the time of patient glucose intake.

19. The system as described in claim 14, wherein said processing means comprises glucose variation means for calculating anticipated glucose variation as a function of said glucose intake data, and wherein said response means comprises comparing means for comparing anticipated glucose variation with measured patient insulin level.

20. The system as described in claim 14, comprising second processing means for processing said ECG signals to obtain a measure of patient glucose, and wherein said response means comprises dual parameter response means for responding as a function of determined insulin and glucose levels.

21. A system for sensing one or more diabetes-related blood constituents of a patient, comprising an implantable apparatus and an external apparatus, said implantable apparatus comprising sensor means for continuously sensing ECG signals from said patient; processing means for continuously processing said ECG signals and obtaining therefrom data indicating the level of at least one selected blood constituent, wherein the processing means include means for comparing the sensed ECG signals against a reference value; and transfer means for transferring said data to said external apparatus, and
said external apparatus comprising indicator means for indicating said patient blood constituent level based upon said transferred data.

22. The system as described in claim 21, wherein said at least one selected blood constituent is blood insulin, and said data is insulin data, and said indicating means comprises display means for displaying a measure of patient blood insulin.

23. The system as described in claim 22, comprising external data transfer means for transferring data from said external apparatus to said implanted apparatus, and wherein said implanted apparatus comprises receiving means for receiving said data transferred from said external apparatus.

24. The system as described in claim 23, wherein said external transfer means comprises means for transferring data representative of patient glucose intake.

25. The system as described in claim 24, wherein said implanted apparatus comprises processing means for processing said insulin data and said glucose intake data, and response means for delivering insulin to said patient based on said insulin data and said glucose data.

26. The system as described in claim 25, wherein said response means comprises an insulin pump for injecting insulin directly into said patient's body.

27. The system as described in claim 23, wherein said external apparatus comprises input means for inputting data representative of patient glucose intake and transfer means for transferring said glucose intake data to said implantable apparatus, said implantable apparatus having receiving means for receiving said transferred glucose intake data.

28. The system as described in claim 21, wherein said blood constituent is glucose and said data is blood glucose data, and said indicating means comprises display means for displaying a measure of patient blood glucose.

29. The system as described in claims 28, comprising validity means for storing data indicative of whether said ECG signals correlate with blood glucose for said patient.

30. The system as described in claim 21, wherein said sensor means comprises means for sensing patient intracardiac signals.

31. The system as described in claim 21, wherein said sensor means comprises means for sensing patient epicardial signals.

32. The system as described in claim 21, wherein said processing means comprises VCG means for deriving the patient VCG from said ECG signals.

33. A system for continuously determining a measure of at least one diabetes-related blood constituent of a patient, said constituent selected from the group of blood insulin and blood glucose, comprising:
sense means for continuously sensing patient ECG signals, the ECG having a QRS portion and a T wave portion;
programmable means for storing data reflective of preselected ECG parameters corresponding to a selected one of said blood constituents;
first signal processing means for substantially continuously extracting from said ECG signals portions representative of said ECG parameters;
second signal processing means for processing said extracted signal portions and obtaining data therefrom which correlates with said selected constituent; and
third signal processing means for continuously determining a measure of said selected constituent as a function of said obtained data wherein said third signal processing means include means for comparing said obtained data against a reference value.

34. The system as described in claim 33, comprising a housing for containing said system whereby said system is adapted to be wearable by a patient.

35. The system as described in claim 33, comprising external means for programming said ECG parameters.

36. The system as described in claim 33, wherein said sense means comprises subcutaneous electrodes.

37. The system as described in claim 33, wherein said first signal processing means comprises averaging means for beat-to-beat averaging over a predetermined number of consecutive patient cardiac beats.

38. The system as described in claim 33, wherein said second signal processing means comprises means for determining from said extracted signals a measure of at least one of the QRS and the T wave portions of said patient ECG signals.

39. The system as described in claim 38, wherein said determining means comprises means for getting a measure of a RMS value of both said QRS and the T wave portions.

40. The system as described in claim 33, wherein said sense means has means for sensing intracardiac patient ECG signals.

41. The system as described in claim 38, further comprising means for storing basal values of preselected ECG parameters, and wherein said determining means comprises statistical means for comprising said determined parameter values with corresponding stored basal values.

42. The system as described in claim 33, wherein said at least one diabetes-related constituent is patient blood insulin, and comprising output means for providing an output representative of patient blood insulin.

43. The system as described in claim 33, wherein said at least one diabetes-related constituent is patient blood glucose, and comprising output means for providing an output representative of patient blood glucose.

44. The system as described in claim 33, wherein said at least one diabetes-related constituent is blood glucose, and further comprising validity means for enabling determination of patient blood glucose.

\* \* \* \* \*